(12) United States Patent
Phuc et al.

(10) Patent No.: US 8,500,879 B2
(45) Date of Patent: Aug. 6, 2013

(54) OXYGEN CONCENTRATOR

(75) Inventors: Tran Ngoc Phuc, Kawaguchi (JP);
Shinichi Nakane, Kawaguchi (JP)

(73) Assignee: Metran Co., Ltd., Saitama (JP)

( * ) Notice: Subject to any disclaimer, the term of this patent is extended or adjusted under 35 U.S.C. 154(b) by 134 days.

(21) Appl. No.: 13/046,977

(22) Filed: Mar. 14, 2011

(65) Prior Publication Data

US 2012/0234173 A1    Sep. 20, 2012

(51) Int. Cl.
*B01D 53/02*    (2006.01)
(52) U.S. Cl.
USPC ............................ 96/113; 95/130; 128/204.18
(58) Field of Classification Search
USPC ............................ 95/130; 96/113; 128/204.18
See application file for complete search history.

(56) References Cited

U.S. PATENT DOCUMENTS

| | | | | |
|---|---|---|---|---|
| 5,002,591 | A * | 3/1991 | Stanford | ............................ 95/98 |
| 5,154,737 | A * | 10/1992 | Jenkins et al. | ...................... 95/11 |
| 6,811,590 | B2 * | 11/2004 | Lee et al. | ............................ 95/98 |
| 2005/0081713 | A1 * | 4/2005 | Lee et al. | ............................ 95/96 |
| 2008/0047435 | A1 * | 2/2008 | Dolensky et al. | ................ 96/116 |
| 2008/0087170 | A1 * | 4/2008 | Deane et al. | ...................... 96/399 |

FOREIGN PATENT DOCUMENTS

| | | | |
|---|---|---|---|
| JP | 2010227517 | A  * | 10/2010 |
| WO | WO/2005/035037 | | 4/2005 |

OTHER PUBLICATIONS

Translation of JP 2010227517 A; Oct. 2010; Japan; Nitta et al.*

* cited by examiner

*Primary Examiner* — Christopher P Jones
(74) *Attorney, Agent, or Firm* — Berenato & White, LLC

(57) ABSTRACT

The present invention provides oxygen concentrators which achieve reliable pressure control in the oxygen columns with reduced number of components for pressure control in the oxygen columns, and also easy maintenance and reduced power consumption. PSA, PVSA, or VSA oxygen concentrator consisting of oxygen concentration columns BF1 and BF2, pressure control means for adjusting pressure in the oxygen concentration columns, and oxygen tank T for storing concentrated oxygen, comprises mechanical flow control means SC1 which regulates flow from the oxygen tank to the oxygen concentration columns. Pressures in the oxygen concentration columns BF1 and BF2 are kept within a predetermined range by the function of mechanical flow control means SC1 placed in between the oxygen concentration columns and the oxygen tank.

2 Claims, 4 Drawing Sheets

OXYGEN CONCENTRATOR

BACKGROUND OF THE INVENTION

1. Field of the Invention

The present invention relates to oxygen concentrators.

2. Description of the Related Art

Recently oxygen concentrators and liquid oxygen are normally used as oxygen supplying methods in the field of home oxygen therapy.

There are many patients with respiratory failure who take treatment with supplemental oxygen at home in the field of home oxygen therapy. Such patients take oxygen that is concentrated to approximately 90%, from home oxygen supply sources which generally include oxygen concentrators and liquid oxygen.

For the oxygen concentrators, ones with the function which adsorbs nitrogen in the air have been developed. This method includes PSA (pressure swing adsorption) in which selective adsorbent for nitrogen is put in the cylinder and oxygen and nitrogen in the air are separated by repetition of pressurization and depressurization, PVSA (pressure vacuum swing adsorption) in which minimum pressure is lower than atmospheric pressure and maximum pressure is larger than atmospheric pressure, and VSA (vacuum swing adsorption) in which maximum pressure is equal to or lower than atmospheric pressure and minimum pressure is lower than atmospheric pressure.

In this type of oxygen concentrators, PSA or PVSA circuit comprises a plurality of oxygen concentration columns (usually two) comprised of oxygen concentrating catalysts such as zeolite, and supplies alternately concentrated oxygen to patients via oxygen tank.

In this regard, PSA or PVSA circuit is connected to the oxygen tank through the flow channel for concentrated oxygen airtight. To supply concentrated oxygen gas at a stable oxygen concentration, the pressure from the said circuit to the oxygen tank (hereinafter referred to as pressure within the system) always needs to be set within a predetermined range depending on the capacity and concentration of oxygen concentrating catalysts and other conditions such as temperature in the oxygen concentration columns.

Previously, pressure control in such system has been conducted by placing control valves in between oxygen concentration columns and the oxygen tank, always monitoring the pressures in oxygen concentration columns and the oxygen tank, and then controlling the valves depending on the monitored pressure (International Publication WO2005/035037 Pamphlet (full text)).

However, many components and means for controlling these components have been required to control pressure in the system in the prior art.

Therefore, the structure becomes complex, and it makes the oxygen concentrator expensive and power consuming. It also makes maintenance of the concentrator difficult.

Accordingly, the task of the present invention is to provide oxygen concentrators which achieve reliable pressure control in the oxygen columns with reduced number of components for pressure control in the oxygen columns and also easy maintenance and reduced power consumption.

Another task of the present invention is to provide oxygen concentrators with high oxygen concentration efficiency.

SUMMARY OF THE INVENTION

The present invention which solves the above-identified problems is a PSA, PVSA, or VSA oxygen concentrator consisting of more than one oxygen concentration columns which concentrate oxygen to predetermined range by adsorbing nitrogen from taken air by swinging high pressure side and low pressure side of the oxygen concentration columns, the pressure control means for adjusting pressure in the said oxygen concentration columns, and the oxygen tank for storing concentrated oxygen. The said oxygen concentrator comprises the first mechanical flow control means placed in between the said oxygen concentration columns and the said oxygen tank. The said first mechanical flow control means regulates flow from the oxygen concentration columns to the oxygen tank, and passes generated concentrated oxygen from the oxygen concentration columns to the oxygen tank when differential pressure between the oxygen concentration columns and the oxygen tank reaches a predetermined range. This allows the pressure in the oxygen concentration columns to be kept in a predetermined range.

The term "mechanical flow control means" used in this specification is means for controlling flow (pressure) by mechanical action such as check valves, preferably with spring, which are distinguished from the control means such as electromagnetic valves which utilize control signals. Specifically, check valves with spring are preferred for the second mechanical flow control means to regulate flow from the oxygen tank to the oxygen concentration columns.

In this way, by placing mechanical flow control means at the desired location, the oxygen concentrator of the present invention allows responsive pressure control in the oxygen columns without controlling such valves like electromagnetic valves which need to correspond to signals from the pressure sensors.

In the specific embodiment of the preset invention, the oxygen concentrator consists of at least one pair of oxygen concentration columns which are composed of the high pressure side and the low pressure side, preferably, the said pair of oxygen concentration columns functions by switching the low pressure side and the high pressure side. More specifically, a valve for providing predetermined amount of generated concentrated oxygen from the high pressure side to the low pressure side when switching is equipped in between the said pair of oxygen concentration columns.

According to the present invention, pressure in oxygen concentration columns can be precisely controlled in a predetermined range just by placing mechanical flow control means such as check valves in between the oxygen concentration columns and the oxygen tank. Thus, the structure for maintaining pressure in the oxygen tank becomes simple, and it allows reduction in the number of components and easy maintenance.

Moreover, the oxygen concentrator of the present invention comprises at least one pair of oxygen concentration columns which are composed of the high pressure side and the low pressure side, and the said pair of oxygen concentration columns functions by switching the low pressure side and the high pressure side. High oxygen concentration efficiency is achieved by providing valves in between the high pressure side and the low pressure side of oxygen concentration columns to supply a predetermined amount of high concentration of oxygen from the high pressure side to the low pressure side when switching the high pressure side and the low pressure side.

BRIEF DESCRIPTION OF THE DRAWINGS

For more complete understanding of the present invention and the advantages hereof, reference is now made to the following description taken in conjunction with the accompanying drawings wherein.

DETAILED DESCRIPTION OF THE EXEMPLARY EMBODIMENTS OF THE INVENTION

Herewith, the embodiment of the present invention will be described with reference to the drawings.

The first embodiment of the oxygen concentrator will be described based on FIGS. 1 and 2.

Figure 1:
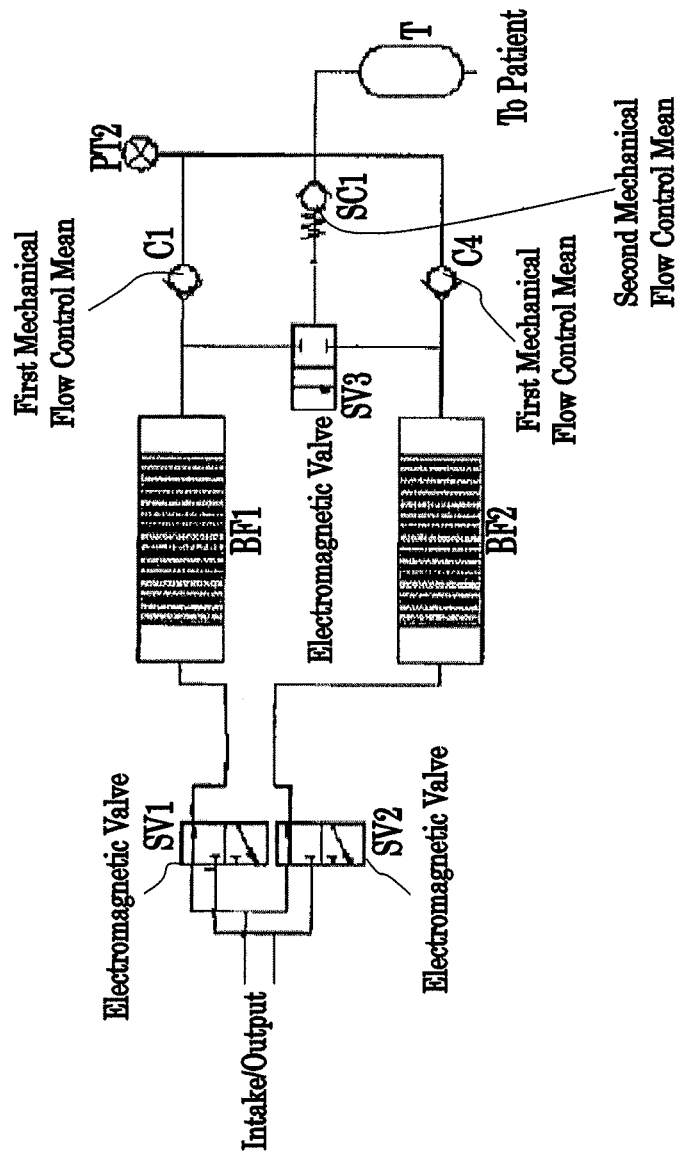
FIG. 1 is a figure showing an example of the oxygen concentrator of the present invention.
Figure 2:
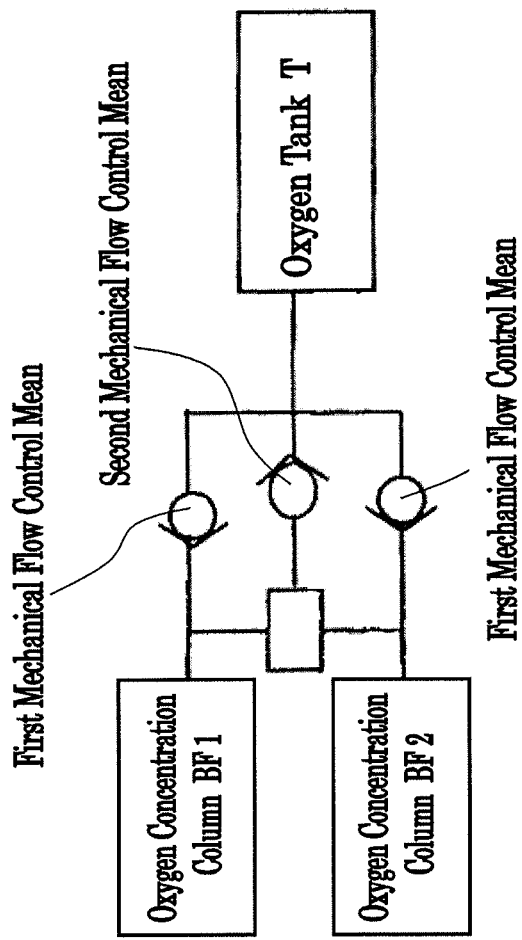
FIG. 2 is a figure showing main components of the oxygen concentrator shown in FIG. 1.

FIG. 1 shows an example of the oxygen concentrator of the present invention, and FIG. 2 shows main components of the oxygen concentrator shown in FIG. 1.

Oxygen concentrator 1 shown in FIG. 1 is a PVSA oxygen concentrator comprising a pair of oxygen concentration columns BF1 and BF2, mainly used for medical purpose. However, the present invention is not restricted to this PVSA medical oxygen concentrator.

As shown in FIG. 1, the oxygen concentrator 1 of the present invention is a device which sends pumped (not shown) air (intake in the figure) via a filter (not shown) to the oxygen concentration column BF1 or BF2, removes nitrogen from the taken air, supplies gas which has high oxygen concentration (oxygen concentrated gas) to oxygen tank T, and then provides concentrated oxygen stored in the oxygen tank T to patients.

In this regard, one of the pair of the oxygen concentration columns BF1 or BF2 is kept at high pressure condition by pressure control means (pressurize) which is not shown in the figure, and the other oxygen concentration column is kept at reduced pressure condition by pressure control means (depressurize). Pressure swing by alternating pressurization and depressurization allows efficient nitrogen removal from air and production of oxygen concentrated gas with desired oxygen concentrations.

Nitrogen is adsorbed from air in the pressurized oxygen concentration column BF1 or BF2 by pressure control means (pressurize) that the oxygen concentration is increased. On the other hand, reproduction of the catalyst is promoted in the oxygen concentration column BF1 or BF2 by desorbing and releasing nitrogen out of the system (Output) in the depressurized oxygen concentration column BF1 or BF2 by pressure control means (depressurize). Moreover, it is common to locate pressure control means for pressurizing the oxygen concentration column before the oxygen concentration column (at the side of intake/output), and the pressure control means for depressurizing the oxygen concentration column after the oxygen concentration column as in prior art.

In this way, oxygen concentrator 1 of the present invention can always provide stable oxygen concentrated gas by alternately repeating production of high concentration oxygen by nitrogen adsorption at the high pressure side of the oxygen concentration column, and reproduction of catalyst by nitrogen desorption at the low pressure side of the oxygen concentration column.

Concentrated oxygen gas generated at the high pressure side of the oxygen concentration column is sent to oxygen tank T and then stored in oxygen tank T. The concentrated oxygen gas stored in this way is used as the oxygen supply source for intended purposes (To Patient, in FIG. 1).

The catalysts used for the oxygen concentration columns BF1 and BF2 are not specifically restricted as long as the object of the present invention is achieved. Catalysts known in this technical field such as zeolite can be selected depending on the purpose and use.

The embodiment shown in FIG. 1 is an example of a medical PVSA oxygen concentrator comprising a pressurizer and a depressurizer (pressure control means, not shown), and three electromagnetic valves SV1, SV2, and SV3 for switching pressures in the oxygen concentration columns as in the oxygen concentrator of the prior art.

Furthermore, the oxygen concentrator shown in FIG. 1 comprises components like filter for removing impurities from taken air, heat exchanger for keeping temperature of taken air in a predetermined range, silencer for reducing noise generated in the device, flow channel for releasing desorbed nitrogen out of the device, and silencer placed on the said flow channel as in the oxygen concentrator of the prior art as necessary.

The concentrated oxygen generated in the oxygen concentration columns BF1 and BF2 is stored in oxygen tank T, and then sent to users such as patients depending on the intended use.

Internal pressures and oxygen concentrations are monitored by various sensors, for instance, an oxygen sensor, a flow sensor, and a differential pressure sensor (not shown) located after the oxygen tank.

In addition to these oxygen concentrators of the prior art, the oxygen concentrator of the embodiment shown in FIGS. 1 and 2 comprises check valve SC1 placed in between the oxygen concentration columns and the oxygen tank as the second mechanical flow control means for controlling pressure in the oxygen concentration columns in a predetermined range.

As shown in FIG. 2, oxygen concentrator 1 of this embodiment comprises check valve with spring (relief check valve) SC1 which regulates gas flow from oxygen tank T to oxygen concentration columns BF1 and BF2.

By placing check valves at the predetermined point in this way, oxygen concentrator 1 of this embodiment automatically adjusts the pressure in oxygen concentration columns BF1 and BF2 in a predetermined range. That is, control of gas flow by these check valves in addition to pressurization and depressurization of the oxygen concentration columns by a pressurizer and a depressurizer allows pressures in the oxygen concentration columns to be always kept in a predetermined range (automatically).

Specifically, by placing spring check valve SC1 in between oxygen concentration columns BF1, BF2 and oxygen tank T, pressures in the oxygen concentration columns BF1 and BF 2 can be automatically controlled.

More specifically, spring check valve SC1 regulates gas flow from oxygen tank T to oxygen concentration columns BF 1 and BF 2, and also allows flow of concentrated oxygen gas from oxygen concentration column BF1 or BF2 to oxygen tank T only when the differential pressure between oxygen concentration column BF1 or BF2 (pressurized side) which generates concentrated oxygen and oxygen tank T reaches a predetermined range. Therefore, generated concentrated oxygen gas is not allowed to flow to oxygen tank T when the pressure of the pressurized oxygen concentration column BF1 or BF2 is below a predetermined range. Thus, the pressure in oxygen concentration column BF1 or BF2 is always kept in a predetermined range.

Check valves C1 and C4 regulate gas flow from oxygen concentration columns BF1 and BF2 to oxygen tank T respectively. In the oxygen concentrator of the first embodiment of the present invention composed in this way, the function of spring check valve SC1 always allow to keep the pressure in the oxygen concentration columns in a predetermined range without special control circuit or control device.

Therefore, the monitoring means for monitoring the pressure in the oxygen concentration columns and the control means for controlling the pressure can be removed. Moreover, maintenance will be easy since the pressure in the oxygen concentration columns can always be kept in a predetermined range with a simple structure.

Figure 3:
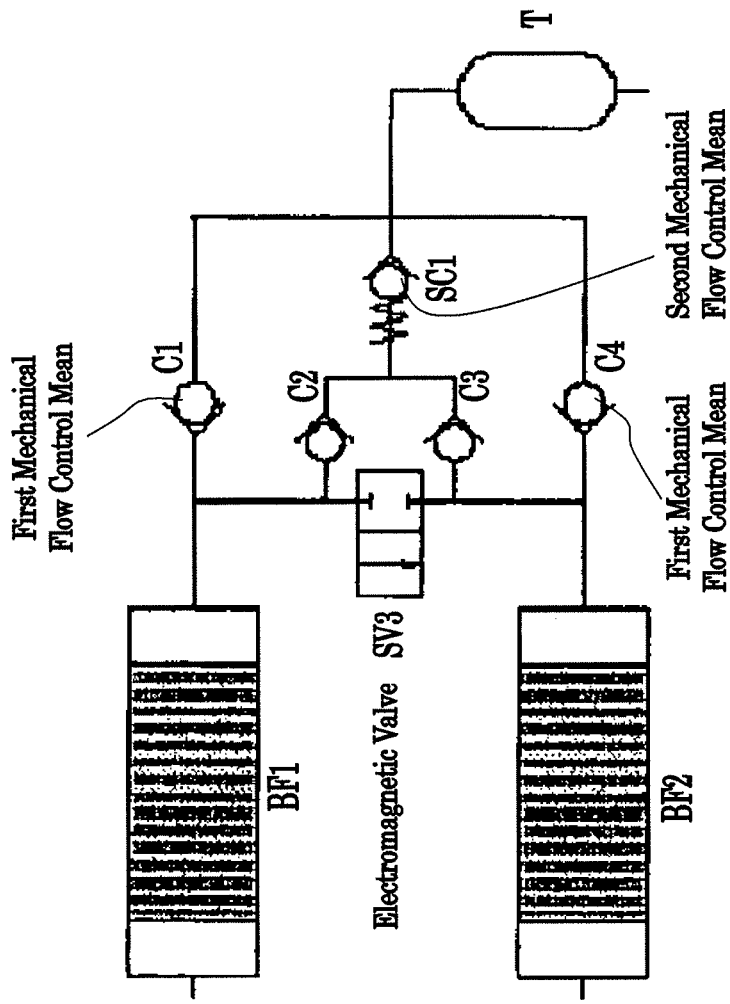
FIG. 3 is a figure showing main components of the oxygen concentrator of another embodiment.

The second embodiment of the present invention will be described based on FIG. 3. FIG. 3 shows the main components of the oxygen concentrator of the second embodiment of the present invention.

The oxygen concentrator of the second embodiment is the same as the first embodiment shown in FIGS. 1 and 2 except that the second embodiment has a structure that a predetermined amount of concentrated oxygen is supplied from the high pressure side to the low pressure side of a pair of a oxygen concentration columns when the high pressure side and the low pressure side is switched.

Therefore, the description of the detail is omitted to avoid repetition, and the identical reference numerals are assigned to the identical components.

As shown in FIG. 3, the oxygen concentrator of this embodiment supplies predetermined amount of concentrated oxygen from the high pressure side of the oxygen concentration columns (e.g. BF1) to the low pressure side of the oxygen concentration columns (e.g. BF2) right after switching of the PVSA cycle.

Therefore, switching valve SV2 keeps the flow channel from the high pressured oxygen concentration column to the low pressured oxygen concentration column open for a predetermined time, for instance, a few ms to a few hundred ms, when the PVSA cycle is switched.

The amount introduced can be arbitrarily determined depending on the specification of oxygen concentration columns BF1 and BF2 (size, performance of oxygen concentration, etc.).

In this way, pressure rising time at the low pressured oxygen concentration column can be accelerated that oxygen can be efficiently concentrated.

In this regard, check valves C2 and C3 have a function to prevent leaks of concentrated oxygen gas from the high pressure side to the low pressure side of the oxygen concentration columns.

The oxygen concentrator of the second embodiment of the present invention composed in this way can always keep the pressure in the oxygen concentration columns in a predetermined range without special control circuit or control device due to the function of check valve SC1 as in the first embodiment, and can also maintain high oxygen concentration efficiency by introduction of predetermined amount (predetermined pressure) of concentrated oxygen from the high pressure side to the low pressure side of the oxygen concentration columns when the PVSA cycle is switched.

Even in such composition, the pressure in a pair of oxygen concentration columns can be maintained by the function of check valve SC1.

The embodiments of the oxygen concentrators of the present invention were described. The present invention is not restricted to the above-stated embodiments and can widely be applied. For instance, the oxygen concentrators of the first and the second embodiment shown in the FIGS. 1 to 3 are for home medical care, however, the power sources can arbitrarily be changed.

For example, it can be used as a portable oxygen concentrator by driving the oxygen concentrator of the present invention with internal batteries. It can also be used as an oxygen supply source of oxygen supply device such as artificial respirators.

Moreover, it can also be used as an oxygen supply source for generating relatively low concentration of oxygen for home care by changing the capacity of nitrogen adsorbing catalysts.

Figure 4:
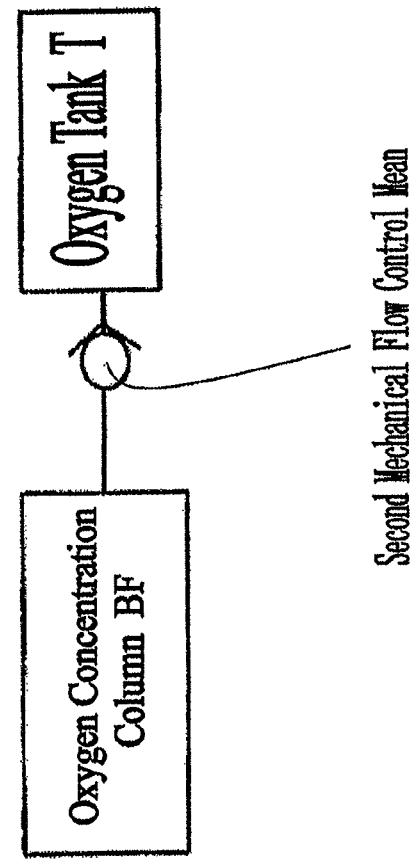
FIG. 4 is a figure showing the basic structure of the main components of the oxygen concentrator of the present invention.

Furthermore, mainly PVSA oxygen concentrators with a pair of oxygen concentration columns were described in the above embodiments, however, the number of oxygen concentration columns is not restricted that it can be more than one. Also, it is not restricted to PVSA, but can be PSA and VSA oxygen concentrators. As shown in FIG. 4, it is within the scope of the present invention as long as the second mechanical flow control means is placed in between oxygen concentration columns BF and oxygen tank T for regulation of flow from the oxygen tank to the oxygen concentration columns. FIG. 4 shows the basic structure of the main components of the oxygen concentrators of the present invention.

Moreover, the number of oxygen tank T can be more than one, though it was one in the above-described embodiments. Although pressure in the oxygen concentration columns is switched by three electromagnetic valves SV1, SV2, and SV3 in the above-embodiments, rotary valves can be used instead of electromagnetic valves.

What is claimed is:

1. A PSA, PVSA, or VSA oxygen concentrator comprising at least one pair of oxygen concentration columns for concentrating oxygen to a predetermined range by switching high pressure side and low pressure side of the oxygen concentration columns to adsorb nitrogen from taken air;
   a pressure controlling means for adjusting pressure of the oxygen concentration columns; and
   an oxygen tank for storing generated concentrated oxygen;
   the oxygen concentrator comprising:
   a first mechanical flow control means individually placed on a plurality of first channels which are extended from each of the at least one pair of oxygen concentration columns, and connected to the oxygen tank, allowing flow from the oxygen concentration columns to the oxygen tank and prohibiting flow from the oxygen tank to the oxygen concentration columns;
   at least one first check valve with spring placed on a second channel extended from the oxygen tank to the at least one pair of oxygen concentration columns distinguished from the first channels, prohibiting flow from the oxygen concentration columns to the oxygen tank and allowing excess oxygen which cannot be contained in the oxygen tank to escape from the high pressure side of the oxygen concentration columns to the low pressure side of the oxygen concentration columns; and
   second check valves individually placed on a plurality of third channels branched from the second channel extended from the oxygen tank and connected to each of the at least one pair of oxygen concentration columns, allowing flow from the oxygen tank to the oxygen concentration columns and prohibiting flow from the oxygen concentration columns to the oxygen tank.

2. The oxygen concentrator according to claim 1, wherein said first mechanical flow control means is disposed in parallel with said at least one first check valve, and said first check valve is connected in series with said second check valves.

* * * * *